US00PP08167P

United States Patent [19]

van der Knaap

[11] Patent Number: Plant 8,167

[45] Date of Patent: Mar. 2, 1993

[54] CHRYSANTHEMUM PLANT — SNOW BIJOUX CULTIVAR

[75] Inventor: Jacques C. M. van der Knaap, De Lier, Netherlands

[73] Assignee: Fides Beheer B.V., De Lier, Netherlands

[21] Appl. No.: 721,712

[22] Filed: Jun. 26, 1991

[51] Int. Cl.[5] ..... A01H 5/00

[52] U.S. Cl. ..... Plt./82.1

[58] Field of Search ..... Plt./74.1, 82.1, 76

[56] References Cited

U.S. PATENT DOCUMENTS

P.P. 6,241 8/1988 van der Knaap ..... Plt. 76

*Primary Examiner*—Howard J. Locker

*Attorney, Agent, or Firm*—Burns, Doane, Swecker & Mathis

[57] ABSTRACT

A new and distinct cultivar of Chrysanthemum plant named Snow Bijoux is provided. The new culivar is a spontaneous mutation of the Bijoux cultivar (U.S. Plant Pat. No. 6,241). More specifically, the new cultivar forms attractive white flowers of the spider anemone type having a yellow center. The white tubular ray florets of the Snow Bijoux cultivar (as illustrated) can be readily distinguished from those of the Bijoux cultivar which are soft pink in coloration. The inflorescence tends to be relatively flat in configuration when mature. The response period of the flowers is approximately nine weeks. The new cultivar is particularly suited for use in the production of a cut spider anemone spray under greenhouse conditions.

1 Drawing Sheet

SUMMARY OF THE INVENTION

The present invention comprises a new and distinct cultivar of Chrysanthemum, botanically known as *Chrysanthemum morifolium*, Ramat., and hereinafter is referred to by the cultivar name Snow Bijoux.

The new Snow Bijoux cultivar is a spontaneous mutation of unknown causation which was discovered and carefully preserved during the course of plant selection work which was conducted by me. The new cultivar was discovered during April, 1987 among plants of the Bijoux cultivar (U.S. Plant Pat. No. 6,241) being grown under my direct supervision at De Lier, The Netherlands.

It was observed that a plant consistently formed flowers having cream white ray florets with a yellow flower center which are considerably different in coloration than those of the Bijoux cultivar wherein the tubular ray florets are soft pink in appearance. The other characteristics of this plant were found to be substantially identical to those of the Bijoux cultivar. Had I not discovered, carefully studied, and preserved this new cultivar, it would have been lost to mankind. This new cultivar is particularly well suited for growing in the production of a cut spider anemone spray.

It was found that the new cultivar of the present invention:

(a) exhibits attractive spider anemone flowers having an overall diameter of approximately 60 mm. wherein the tubular ray florets are white and the disc florets are yellow in coloration, said flowers being distinguishable from those of the Bijoux cultivar wherein the tubular ray florets are soft pink, (b) bears flowers in a generally flat capitulum form when mature, (c) exhibits a flower response period of approximately nine weeks, (e) forms attractive dark green foliage, and (e) has the ability to produce flowers of commercially acceptable quality throughout the year in a cut mum production program.

Asexual reproduction of the new cultivar by cuttings as performed at De Lier, The Netherlands, in a controlled environment has demonstrated that the characteristics of the new cultivar as herein disclosed are firmly fixed and are retained through successive generations of asexual propagation.

Snow Bijoux has not been observed under all possible environmental conditions to date. Accordingly, it is possible that the phenotype may vary somewhat with variations in the environment, such as temperature, light, day length, contact with pesticides and/or subjection to growth retardant treatments.

When the new cultivar of the present invention is compared to the Yellow Bijoux cultivar (U.S. Ser. No. 721,393, filed concurrently herewith), it is noted that the Snow Bijoux cultivar exhibits white tubular ray florets and the Yellow Bijoux cultivar exhibits dissimilar yellow ray florets which also are tubular in configuration.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at De Lier, The Netherlands.

DETAILED DESCRIPTION

The chart used in the identification of colors described hereafter is the R.H.S. Colour Chart of The Royal Horticultural Society, London, England. The color values were determined at 11:00 a.m. to 12:00 noon under natural daylight conditions at De Lier, The Netherlands, during May, 1991. The plants described were grown under standard greenhouse conditions which approximate those commonly utilized for the production of cut mums.

Classification:

*Botanical.*—*Chrysanthemum morifolium* Ramat., cv. Snow Bijoux.

*Commercial.*—Cut spider anemone spray.

INFLORESCENCE

A. Capitulum:

*Form.*—Generally flat when mature.

*Type.*—Spider anemone.

*Diameter across face.*—Approximately 60 mm. on average.

B. Corolla of ray and disc florets:

*Color (general tonality from a distance of three meters).*—White with some darkening at center.

*Color ray florets. (top surface).*—White, White Group 155D.

*Color disc florets.*—Yellow, Yellow Group 10A to 10C.

C. Reproductive organs

*Androecium.*—Only rudimentary in disc florets.

*Gynoecium.*—Present in both ray and disc florets.

PLANT

A. General appearance:

*Height.*—Approximately 80 cm. on average.

B. Foliage:

*Color (upper surface).*—Yellow-Green Group 147A.

*Color (under surface).*—Yellow-Green Group 147B.

I claim:

1. A new and distinct cultivar of Chrysanthemum plant named Snow Bijoux substantially as herein shown and described, which:

(a) exhibits attractive spider anemone flowers having an overall diameter of approximately 60 mm. wherein the tubular ray florets are white and the disc florets are yellow in coloration, said flowers being distinguishable from those of the Bijoux cultivar wherein the tubular ray florets are soft pink, (b) bears flowers in a generally flat capitulum form when mature, (c) exhibits a flower response period of approximately nine weeks, (d) forms attractive dark green foliage, and (e) has the ability to produce flowers of commercially acceptable quality throughout the year in a cut mum production program.

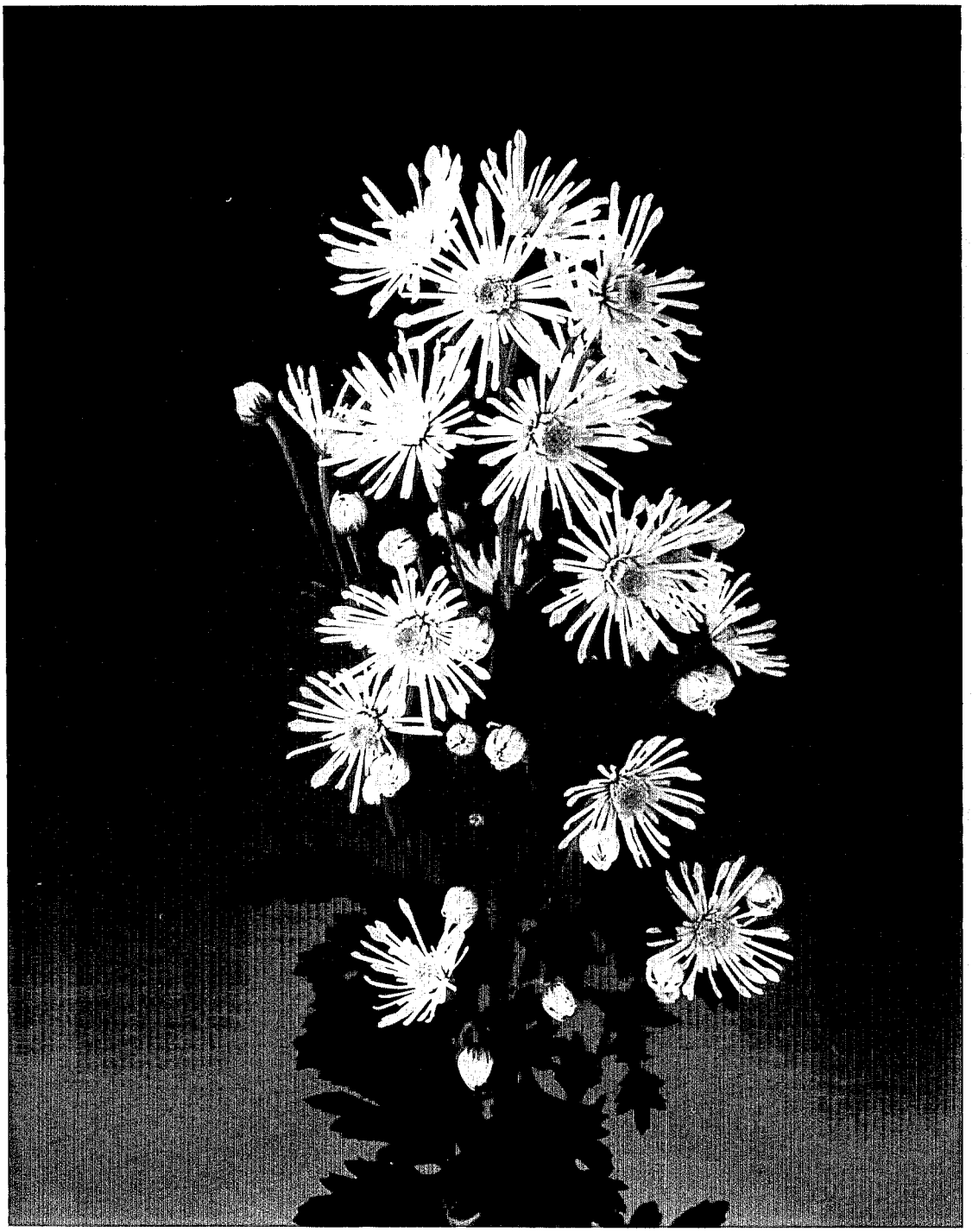

* * * * *